United States Patent [19]
Greidinger et al.

[11] 3,936,501
[45] Feb. 3, 1976

[54] PROCESS FOR THE MANUFACTURE OF CRYSTALLINE UREA PHOSPHATE
[75] Inventors: Dahlia Simeona Greidinger; Benedict Cytter, both of Haifa, Israel
[73] Assignee: Chemicals & Phosphates, Ltd., Haifa, Israel
[22] Filed: May 7, 1974
[21] Appl. No.: 467,670

[30] Foreign Application Priority Data
June 29, 1973 Israel.................................... 42624

[52] U.S. Cl............................................ 260/555 R
[51] Int. Cl.²....................................... C07C 126/00
[58] Field of Search ................................ 260/555 R

[56] References Cited
OTHER PUBLICATIONS
Shamshurin, "The Synthesis of Urea Phosphate" (1966) Chemical Abstracts Vol. 65, p. 11833.

Primary Examiner—James O. Thomas, Jr.
Assistant Examiner—A. Siegel
Attorney, Agent, or Firm—John S. Roberts, Jr.

[57] ABSTRACT

The present invention relates to a process for the direct manufacture of crystalline urea phosphate. The process consists in the reaction of solid urea with ortho-phosphoric acid in a substantially anhydrous form. A concentrated phosphoric acid with above 90% by weight $H_3PO_4$ can be used as starting reagent. A preheating of the phosphoric acid at 60°–90°C is preferred in order to induce the spontaneous reaction with the solid urea. The urea phosphate product obtained is ready for use without any further operation. Desired micronutrients such as Mg, Co, Fe, Zn, Cu, Mn may be incorporated in the initial orthophosphoric acid prior to the reaction with the solid urea.

5 Claims, No Drawings

PROCESS FOR THE MANUFACTURE OF CRYSTALLINE UREA PHOSPHATE

The present invention concerns the manufacture of crystalline urea phosphate by the direct reaction of urea with ortho-phosphoric acid.

Urea phosphate is a valuable product with great potential as a fertilizer and as a feed additive mainly for cattle. Recently, urea phosphate was also successfully used as a speciality cleaner and as an active ingredient in some detergent compositions.

The process of urea phosphate production by which aqueous wet process phosphoric acid containing up to 69% $H_3PO_4$ is reacted with an aqueous solution of urea (70% urea), is known from U.S. Pat. No. 1,149,924. The reaction product consists of a highly concentrated aqueous solution of urea phosphate from which urea phosphate is crystallized and separated. The crystals of urea phosphate, separated from the mother liquor have to be dried very carefully, below 70°C, as otherwise the solid crystalline mass becomes fluid and undergoes decomposition. Similarly the recovery of the mother liquor has to be effected under rigorously controlled conditions in order to avoid hydrolysis. Therefore, this known process is characterized by the complicated and expensive equipment required for the recovery of crystalline urea phosphate.

In the U.S.S.R., a process was recently reported (Phosphorus and Potassium, 52, 1971) for the manufacture of a granular urea phosphate by the reaction of polyphosphoric acid and urea. It specifies that the flow-rate of the reactants is controlled in order to obtain products with various ratios of N:P. The product obtained can be used mainly as fertilizer in view of its granular form. As known urea phosphate in a granular form is unsuitable for animal feed.

It is one of the objects of the present invention to obtain crystalline urea phosphate from urea and ortho-phosphoric acid. Another object of the present invention is directly to obtain crystalline urea phosphate from urea and ortho-phosphoric acid without the further processing and recovery problems normally encountered in the crystalline urea phosphate production. These and other objects which may appear as this specification proceeds, are achieved by this invention.

The invention consists of a process for the direct manufacture of crystalline urea phosphate, characterized in that solid urea is reacted with ortho-phosphoric acid in a substantially anhydrous form. The invention is based on the surprising observation that when solid urea is reacted with a stoichiometric amount of anhydrous ortho-phosphoric acid, a spontaneous complete addition reaction occurs which results directly in dry crystalline urea phosphate which does not require any further processing or recovery problems. By a microscopic investigation of the course of reaction, it was found that the reactants, solid urea and anhydrous ortho-phosphoric acid, pass through a stage where the crystals of urea are suspended in the syrupy mass of anhydrous ortho-phosphoric acid without at any stage forming a clear transparent solution. Monocrystalline urea phosphate crystals of the orthorhombic system are suddenly formed in this syrupy mass without the necessity of any further separation operation. By a thorough further investigation of the reaction involved between the solid urea and ortho-phosphoric acid it was unexpectedly found that up to 7% by weight water may be present in the reaction system, this amount of water being expelled during the exothermic reaction between the urea and the ortho-phosphoric acid. Thus for example, when the reaction was carried out with ortho-phosphoric acid of 92.5% $H_3PO_4$ (wt. per cent) and solid urea, in stoichiometric amounts, which corresponds to a water content of about 5% by weight in the reaction system, the resulting product was crystalline urea phosphate which contains only 0.4% water. These crystals of urea phosphate were identical to the urea phosphate crystals obtained from anhydrous ortho-phosphoric acid, in their main composition and microscopial appearance. This unexpected observation enables replacement of the anhydrous ortho-phosphoric acid which is not a common commercially available reagent by concentrated ortho-phosphoric acid having a concentration above 90% $H_3PO_4$ by weight, in the reaction with solid urea for the present invention. This concentrated ortho-phosphoric acid is normally obtained from the elemental phosphorous or by liquid - liquid extraction of phosphoric acid solutions. These grades of ortho-phosphoric acid are, characterized by their high degree of purity which yields a pure urea phosphate, virtually free of heavy cations. This is very important when used as animal feed.

Also available on the market is the so-called superphosphoric acid, which contains $P_2O_5$ in addition to $H_3PO_4$, which has a $P_2O_5$ content of over 72% $P_2O_5$. When experiments were performed with this type of superphosphoric acid and stoichiometric amounts of solid urea under the same conditions as for the present invention, no crystalline urea phosphate was obtained. The resulting product was a sticky "honey" mass which did not crystallize and took several days to solidify. The mechanism which would explain the reasons why superphosphoric acid does not react with solid urea to give crystalline urea phosphate is not fully understood. Many theories could perhaps be presented to explain this phenomenon, but these would be beyond the scope of the present invention.

The molar ratios between the urea and ortho-phosphoric acid is 1:1; a small excess of urea may be present without interfering in the direct preparation of the crystalline urea phosphate but an excess of ortho-phosphoric acid should be avoided.

The process according to the invention can be carried continuously by the constant feed of molar (1:1) ratios of ortho-phosphoric acid and the solid urea to an apparatus in which the reactants are mixed and at the same time conveyed onward e.g., by means of a pug-mill. Of course, any other suitable mixer system can be used and it is not necessary that the mixing be done simultaneously with the onward conveying; the reactants may dwell in the mixer for a time and the entire product then be discharged from the mixer at once. It is preferable, however, that a continuous mixing of the reagents be provided in order to obtain a better contact between them and to avoid agglomerating of the urea phosphate crystals. In order to improve the free-flowing properties of the urea phosphate crystals, a common anti-caking agent such as amorphous silica, bentonite, flour, etc., may be added. The amount of the anti-caking agent is in the usual range utilized for this purpose such as between 1.50 – 3% by weight.

The process is very simple to carry out; starting with anhydrous ortho-phosphoric acid, which is crystalline at room temperature, a slight heating transforms the crystals into a clear liquid solution. In order to induce the spontaneous reaction with the solid urea, a preheating of the anhydrous ortho-phosphoric acid at 60°–90°C is preferred. After mixing with the solid urea, the reaction system has to be vigorously cooled in view of the exothermic reaction which takes place. The reaction is accomplished after a few seconds and dry crystalline urea phosphate formed in the reaction vessel is ready for use without any further operation. When starting with concentrated ortho-phosphoric acid, which has a concentration of over 90% $H_3PO_4$ (wt. per cent), the reaction according to the invention can be carried out in two ways. According to one preferable procedure the two reactants, in which the ortho-phosphoric acid (above 90% by wt. $H_3PO_4$) is previously preheated at 60°–90°C, are mixed. The water present in the initial ortho-phosphoric acid is expelled during the prior heating and exothermal reaction with the solid urea. By another procedure the initial concentrated ortho-phosphoric acid (above 90% $H_3PO_4$) is first transformed into the anhydrous form and thereafter reacted with the solid urea. The final product in both procedures was the same as in the case of anhydrous ortho-phosphoric acid, and containing only between 0.3% and 0.7% water.

The urea to be used as a starting material in the reaction according to the invention may be any solid urea form commercially available such as prills or crystals or the like.

When the crystalline urea phosphate is for fertillizer or cattle feed use, desired micronutrients such as Mg, Co, Fe, Zn, Cu, Mn, etc., may be incorporated in the initial ortho-phosphoric acid prior to the reaction with the solid urea without interfering the course of reaction. This is an additional advantage over the urea phosphate produced in an aqueous media by crystallization, where a reliable dosage of micronutrients is not possible.

If desired to obtain compounds with a higher ratio of N:P or N:P:K fertilizers, the crystalline urea phosphate may be transformed into prills by adding some more urea or potassium salts. It can also be used in various compound fertilizers where impurity-free, ballast-free, high analysis completely water soluble fertilizers are required.

In order to further illustrate the nature of this invention and the manner of practicing it more fully, the following examples are presented for clearness of understanding only, and no limitation should be understood therefrom since modifications will be obvious to those skilled in the art.

EXAMPLE 1

An amount of 8.5 kgs. of crystals of anhydrous ortho-phosphoric acid (produced by Fluka) was heated at 70°C where it became a fluid syrup. The anhydrous ortho-phosphoric acid solution was fed simultaneously with 5.3 kgs. of urea prills into a continous pug-mill type mixer. The exothermic reaction between the two reactants started immediately. By vigorous cooling, the reaction temperature was kept at 85°–90°C. The reaction mixture became a non-transparent fluid syrup from which crystalline urea phosphate resulted, as the reaction mixture moved forward. An amount of 300 grams of amorphous silica as anti-caking reagent was added and 14.1 kgs. of free-flowing crystalline urea phosphate product poured directly into a bag. The product contained 16.8%N and 18.8%P.

EXAMPLE 2

An amount of 11.2 kgs. of ortho-phosphoric acid of 92.5% $H_3PO_4$ (wt. per cent) obtained by liquid-liquid extraction of phosphoric acid solution was preheated at 70°C and fed simultaneously with 6.3 kgs. of urea prills into a continuous pug-mill type mixer system, and continued as in the previous example. The same reaction as described in the previous example occurred here. The final product contained 16.8%N, 18.6%P amd 0.4% $H_2O$, being of the same quality and appearance as in the previous example.

EXAMPLE 3

Example 2 was repeated using the same amounts and equipment, the only difference being the use of 5 kgs. urea crystals instead of urea prills. As in Example 2, the same product, having identical compsition and appearance, was obtained.

EXAMPLE 4

The following micronutrients: 200 g Fe in form of ferrous sulphate, 0.2 g Co as cobaltous sulphate, 20 g Cu as copper sulphate, 40 g Mn as manganous sulphate and 80 g Zn as zinc sulphate were dissolved in 11.2 kgs. of ortho-phosphoric acid of 92.5% by weight and reacted with 6.3 kgs. of urea prills as in Example 2. The final product contained 16.5%N, 18.2%P, 1.1%Fe, 0.0011%Co, 0.11%Cu, 0.22%Mn and 0.44%Zn.

EXAMPLE 5

The following micronutrients: 200 g Mg in form of magnesium oxide (magnesium hydroxide and magnesium sulphate were also experimented), 100 g Fe in form of ferrous hydroxide (ferrous sulphate, ferric hydroxide and ferric sulphate were also experimented), 0.2 g Co as cobaltous sulphate, 40 g Mn as manganous sulphate and 80 g Zn as zinc oxide (zinc sulphate was also experimented) were dissolved in 11.2 kgs. of ortho-phosphoric acid of 92.5% by weight and reacted with 6.3 kgs. of urea prills as in Example 2. The final product contained 16.5%N, 18.2%P, 0.6%Fe, 1.2%Mg, 0.0011% Co, 0.11%Cu, 0.22%Mn and 0.44%Zn.

We claim:

1. An exothermic process for the direct manufacture of crystalline urea phosphate characterized in that solid urea is reacted stoichiometrically in equimolar quantities with orthophosphoric acid at a temperature of about 60°–90°C wherein said orthophosphoric acid contains above 90% $H_3PO_4$ by weight.

2. A process for the direct manufacture of crystalline urea phosphate according to claim 1, characterized in that the preheated ortho-phosphoric acid is admixed with solid urea.

3. A process for the direct manufacture of crystalline urea phosphate according to claim 1, wherein the ortho-phosphoric acid is first transformed into an anhydrous form and thereafter reacted with solid urea.

4. A process for the direct manufacture of crystalline urea phosphate according to claim 1, being carried out as a a continuous process by the constant feed of molar (1.1) proportions of ortho-phosphoric acid and solid urea into an apparatus in which the reactants are mixed and at the same time conveyed onward.

5. A process for the direct manufacture of crystalline urea phosphate according to claim 1, wherein the ortho-phosphoric acid is preheated at the start of reaction to about 70°C.

* * * * *